US012577555B2

(12) United States Patent
Masutomi et al.

(10) Patent No.: US 12,577,555 B2
(45) Date of Patent: Mar. 17, 2026

(54) SCREENING METHOD FOR TELOMERASE REVERSE TRANSCRIPTASE (TERT) PHOSPHORYLATION INHIBITORS

(71) Applicant: Kenkichi Masutomi, Tokyo (JP)

(72) Inventors: Kenkichi Masutomi, Tokyo (JP); Mami Yasukawa, Tokyo (JP)

(73) Assignee: Kenkichi Masutomi, Tokyo (JP)

( * ) Notice: Subject to any disclaimer, the term of this patent is extended or adjusted under 35 U.S.C. 154(b) by 1371 days.

(21) Appl. No.: 16/770,693

(22) PCT Filed: Dec. 14, 2018

(86) PCT No.: PCT/JP2018/046169
§ 371 (c)(1),
(2) Date: Jun. 8, 2020

(87) PCT Pub. No.: WO2019/117303
PCT Pub. Date: Jun. 20, 2019

(65) Prior Publication Data
US 2023/0124973 A1 Apr. 20, 2023

(30) Foreign Application Priority Data
Dec. 15, 2017 (JP) ................................. 2017-241157

(51) Int. Cl.
*C12Q 1/48* (2006.01)
*C12N 15/10* (2006.01)

(52) U.S. Cl.
CPC ......... *C12N 15/1055* (2013.01); *C12Q 1/485* (2013.01)

(58) Field of Classification Search
None
See application file for complete search history.

(56) References Cited

U.S. PATENT DOCUMENTS

2007/0105796 A1 5/2007 Wada et al.
2018/0251491 A1 9/2018 Ebben et al.

FOREIGN PATENT DOCUMENTS

WO 2005/110476 11/2005
WO 2012/147918 11/2012
WO 2017/040309 3/2017

OTHER PUBLICATIONS

GenBank Mus musculus & Bos taurus TERT entries (Year: 2009).*
Yasukawa et al (Nature Communications 11:1557 eighteen pages) (Year: 2020).*
Office Action issued Nov. 15, 2022 in corresponding Japanese Patent Application No. 2019-559233, with English translation, 15 pages.
English translation of Examples of cited document WO 2012/147918 (of record) in IDS filed on Sep. 8, 2020, 45 pages.
Kenkichi Masutomi, "Analysis of molecular basis for TERT phosphorylation mechanism and RdRP activation control", 2015 Report for Implementation Status Grants-in-Aid for Scientific Research issued Jun. 1, 2017, full English translation, 4 pages.
International Search Report issued Mar. 12, 2019 in International (PCT) Application No. PCT/JP2018/046169.
Written opinion of the International Searching Authority issued Mar. 12, 2019 in International (PCT) Application No. PCT/JP2018/046169.
"Molecular mechanism to dictate RdRP activity of TERT", Research-status report, 2015, with partial English translation, 3 pages.
Maida et al., "Telomerase reverse transcriptase moonlights: Therapeutic targets beyond telomerase", Cancer Science, 2015, vol. 106, No. 11, pp. 1486-1492.
Okamoto et al., "Maintenance of tumor initiating cells of defined genetic composition by nucleostemin", PNAS, 2011, vol. 108, No. 51, pp. 20388-20393.
Maida et al., "Involvement of Telomerase Reverse Transcriptase in Heterochromatin Maintenance", Molecular and Cellular Biology, 2014, vol. 34, No. 9, pp. 1576-1593.
Maida et al., "De Novo RNA Synthesis by RNA-Dependent RNA Polymerase Activity of Telomerase Reverse Transcriptase", Molecular and Cellular Biology, 2016, vol. 36, No. 8, pp. 1248-1259.

* cited by examiner

*Primary Examiner* — Christopher M Gross
(74) *Attorney, Agent, or Firm* — Wenderoth, Lind & Ponack, L.L.P.

(57) ABSTRACT

The present invention provides a method for screening for a telomerase reverse transcriptase (TERT) phosphorylation inhibitor using TERT or a fragment thereof, and a TERT kinase.

4 Claims, 9 Drawing Sheets
Specification includes a Sequence Listing.

Fig.1B hTERT siRNA #2 hTERT siRNA #1

Negative Control (kDa)
225 —
150 —
102 —
76 —

Fig.1A

λ phosphatase

+

−

(kDa)
225 —
150 —
102 —
76 —

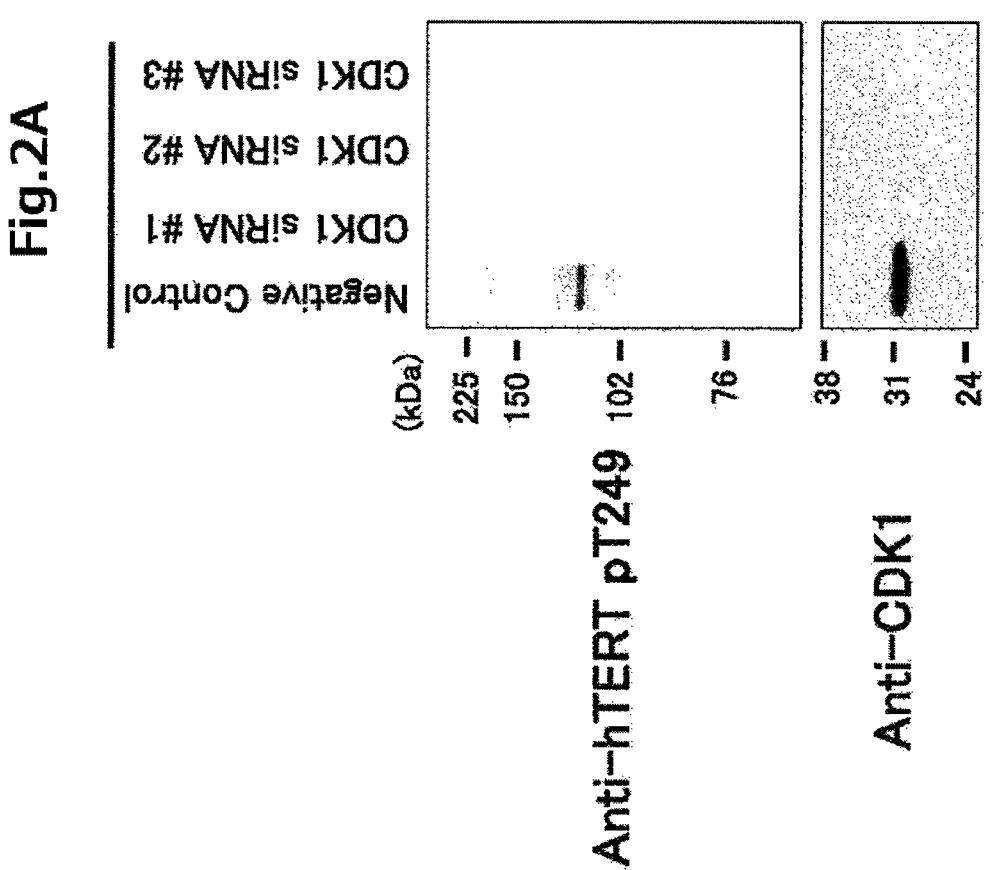

Fig.9
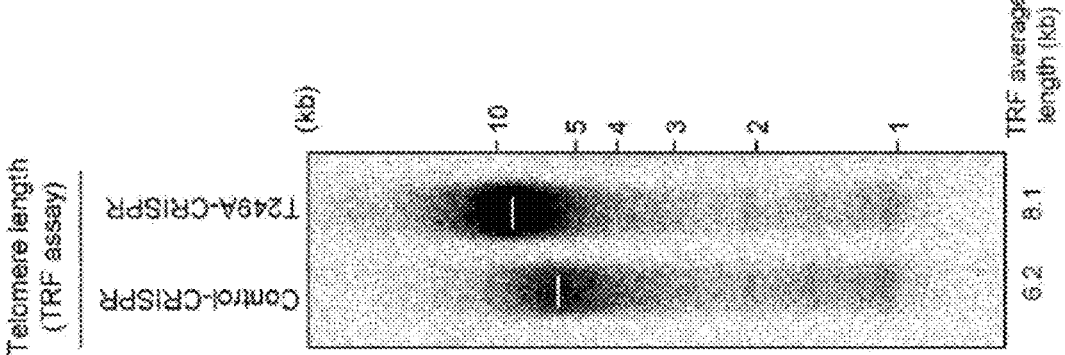
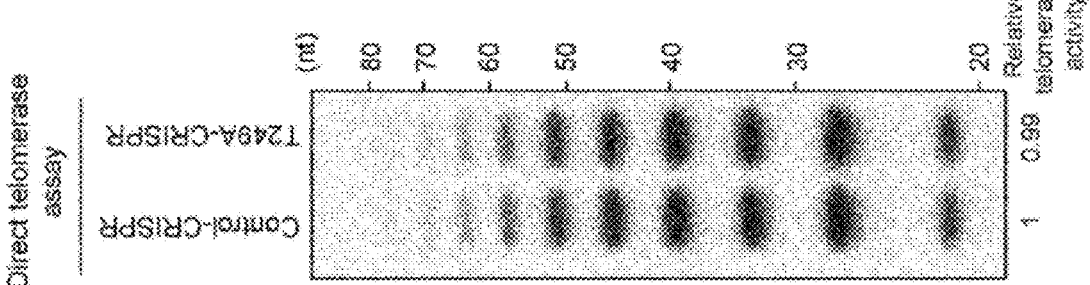
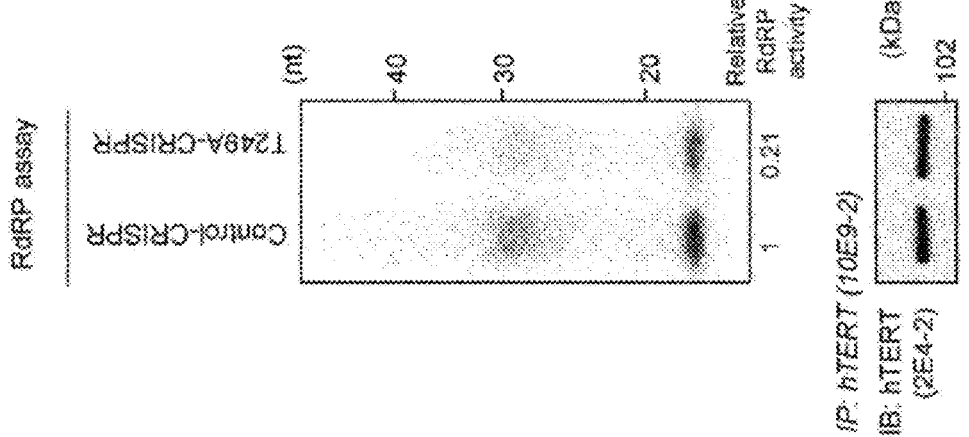

SEQUENCE LISTING

```
<160> NUMBER OF SEQ ID NOS: 20

<210> SEQ ID NO 1
<211> LENGTH: 10
<212> TYPE: PRT
<213> ORGANISM: Artificial Sequence
<220> FEATURE:
<223> OTHER INFORMATION: partial amino acid sequence of hTERT
<220> FEATURE:
<221> NAME/KEY: MOD_RES
<222> LOCATION: (5)..(5)
<223> OTHER INFORMATION: PHOSPHORYLATION

<400> SEQUENCE: 1

Glu Pro Glu Arg Thr Pro Val Gly Gln Gly
1               5                   10

<210> SEQ ID NO 2
```

```
<211> LENGTH: 10
<212> TYPE: PRT
<213> ORGANISM: Artificial Sequence
<220> FEATURE:
<223> OTHER INFORMATION: partial amino acid sequence of hTERT
<220> FEATURE:
<221> NAME/KEY: MOD_RES
<222> LOCATION: (5)..(5)
<223> OTHER INFORMATION: PHOSPHORYLATION

<400> SEQUENCE: 2

Val Gly Gln Gly Ser Trp Ala His Pro Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: partial amino acid sequence of hTERT
<220> FEATURE:
<221> NAME/KEY: MOD_RES
<222> LOCATION: (5)..(5)
<223> OTHER INFORMATION: PHOSPHORYLATION

<400> SEQUENCE: 3

Arg His Arg Val Thr Tyr Val Pro Leu Leu
1               5                   10

<210> SEQ ID NO 4
<211> LENGTH: 10
<212> TYPE: PRT
<213> ORGANISM: Artificial Sequence
<220> FEATURE:
<223> OTHER INFORMATION: partial amino acid sequence of hTERT
<220> FEATURE:
<221> NAME/KEY: MOD_RES
<222> LOCATION: (5)..(5)
<223> OTHER INFORMATION: PHOSPHORYLATION

<400> SEQUENCE: 4

Pro Leu Leu Gly Ser Leu Arg Thr Ala Gln
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Cys binding partial amino acid sequence of
      hTERT
<220> FEATURE:
<221> NAME/KEY: MOD_RES
<222> LOCATION: (6)..(6)
<223> OTHER INFORMATION: PHOSPHORYLATION

<400> SEQUENCE: 5

Cys Glu Pro Glu Arg Thr Pro Val Gly Gln Gly
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Cys binding partial amino acid sequence of
      hTERT
<220> FEATURE:
<221> NAME/KEY: MOD_RES
<222> LOCATION: (6)..(6)
<223> OTHER INFORMATION: PHOSPHORYLATION
```

-continued

```
<400> SEQUENCE: 6

Cys Val Gly Gln Gly Ser Trp Ala His Pro Gly
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Cys binding partial amino acid sequence of
      hTERT
<220> FEATURE:
<221> NAME/KEY: MOD_RES
<222> LOCATION: (6)..(6)
<223> OTHER INFORMATION: PHOSPHORYLATION

<400> SEQUENCE: 7

Cys Arg His Arg Val Thr Tyr Val Pro Leu Leu
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Cys binding partial amino acid sequence of
      hTERT
<220> FEATURE:
<221> NAME/KEY: MOD_RES
<222> LOCATION: (6)..(6)
<223> OTHER INFORMATION: PHOSPHORYLATION

<400> SEQUENCE: 8

Cys Pro Leu Leu Gly Ser Leu Arg Thr Ala Gln
1               5                   10

<210> SEQ ID NO 9
<211> LENGTH: 21
<212> TYPE: DNA
<213> ORGANISM: Artificial Sequence
<220> FEATURE:
<223> OTHER INFORMATION: hTERT siRNA#1

<400> SEQUENCE: 9
gugucugugc ccgggagaat t                                                   21

<210> SEQ ID NO 10
<211> LENGTH: 21
<212> TYPE: DNA
<213> ORGANISM: Artificial Sequence
<220> FEATURE:
<223> OTHER INFORMATION: hTERT siRNA#1

<400> SEQUENCE: 10
uucucccggg cacagacact t                                                   21

<210> SEQ ID NO 11
<211> LENGTH: 21
<212> TYPE: DNA
<213> ORGANISM: Artificial Sequence
<220> FEATURE:
<223> OTHER INFORMATION: hTERT siRNA#2

<400> SEQUENCE: 11
gcauuggaau cagacagcat t                                                   21
```

-continued

<210> SEQ ID NO 12
<211> LENGTH: 21
<212> TYPE: DNA
<213> ORGANISM: Artificial Sequence
<220> FEATURE:
<223> OTHER INFORMATION: hTERT siRNA#2

<400> SEQUENCE: 12
ugcugucuga uuccaaugct t                                                      21

<210> SEQ ID NO 13
<211> LENGTH: 23
<212> TYPE: DNA
<213> ORGANISM: Artificial Sequence
<220> FEATURE:
<223> OTHER INFORMATION: primer for A mutant

<400> SEQUENCE: 13
agccggagcg ggcgcccgtt ggg                                                    23

<210> SEQ ID NO 14
<211> LENGTH: 23
<212> TYPE: DNA
<213> ORGANISM: Artificial Sequence
<220> FEATURE:
<223> OTHER INFORMATION: primer for A mutant

<400> SEQUENCE: 14
cccaacgggc gcccgctccg gct                                                    23

<210> SEQ ID NO 15
<211> LENGTH: 28
<212> TYPE: DNA
<213> ORGANISM: Artificial Sequence
<220> FEATURE:
<223> OTHER INFORMATION: primer for E mutant

<400> SEQUENCE: 15
tgagccggag cgggagcccg ttgggcag                                               28

<210> SEQ ID NO 16
<211> LENGTH: 28
<212> TYPE: DNA
<213> ORGANISM: Artificial Sequence
<220> FEATURE:
<223> OTHER INFORMATION: primer for E mutant

<400> SEQUENCE: 16
ctgcccaacg ggctcccgct ccggctca                                              28

<210> SEQ ID NO 17
<211> LENGTH: 1132
<212> TYPE: PRT
<213> ORGANISM: Homo sapiens

<400> SEQUENCE: 17

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

-continued

```
Pro Pro Ala Ala Pro Ser Phe Arg Gln Val Ser Cys Leu Lys Glu Leu
65              70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
            195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
    275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
            435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
```

-continued

```
                         485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
                515                 520                 525

Val Pro Ala Ala Glu His Arg Leu Arg Glu Glu Ile Leu Ala Lys Phe
        530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
                595                 600                 605

His Arg Glu Ala Arg Pro Ala Leu Leu Thr Ser Arg Leu Arg Phe Ile
                610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
                675                 680                 685

Ala Trp Arg Thr Phe Val Leu Arg Val Arg Ala Gln Asp Pro Pro Pro
        690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
                755                 760                 765

Leu Gln Pro Tyr Met Arg Gln Phe Val Ala His Leu Gln Glu Thr Ser
        770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
                835                 840                 845

Met Glu Asn Lys Leu Phe Ala Gly Ile Arg Arg Asp Gly Leu Leu Leu
        850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910
```

-continued

```
Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                1005

Ala Tyr  Arg Phe His Ala Cys  Val Leu Gln Leu Pro  Phe His Gln
    1010                1015                1020

Gln Val  Trp Lys Asn Pro Thr  Phe Phe Leu Arg Val  Ile Ser Asp
    1025                1030                1035

Thr Ala  Ser Leu Cys Tyr Ser  Ile Leu Lys Ala Lys  Asn Ala Gly
    1040                1045                1050

Met Ser  Leu Gly Ala Lys Gly  Ala Ala Gly Pro Leu  Pro Ser Glu
    1055                1060                1065

Ala Val  Gln Trp Leu Cys His  Gln Ala Phe Leu Leu  Lys Leu Thr
    1070                1075                1080

Arg His  Arg Val Thr Tyr Val  Pro Leu Leu Gly Ser  Leu Arg Thr
    1085                1090                1095

Ala Gln  Thr Gln Leu Ser Arg  Lys Leu Pro Gly Thr  Thr Leu Thr
    1100                1105                1110

Ala Leu  Glu Ala Ala Ala Asn  Pro Ala Leu Pro Ser  Asp Phe Lys
    1115                1120                1125

Thr Ile  Leu Asp
    1130

<210> SEQ ID NO 18
<211> LENGTH: 21
<212> TYPE: PRT
<213> ORGANISM: Artificial Sequence
<220> FEATURE:
<223> OTHER INFORMATION: patial sequence from 241 to 261

<400> SEQUENCE: 18

Gly Ala Ala Pro Glu Pro Glu Arg Thr Pro Val Gly Gln Gly Ser Trp
1               5                   10                  15

Ala His Pro Gly Arg
            20

<210> SEQ ID NO 19
<211> LENGTH: 11
<212> TYPE: PRT
<213> ORGANISM: Artificial Sequence
<220> FEATURE:
<223> OTHER INFORMATION: patial sequence from 1087 to 1097

<400> SEQUENCE: 19

Val Thr Tyr Val Pro Leu Leu Gly Ser Leu Arg
1               5                   10

<210> SEQ ID NO 20
<211> LENGTH: 23
<212> TYPE: DNA
```

-continued

```
<213> ORGANISM: Artificial Sequence
<220> FEATURE:
<223> OTHER INFORMATION: guide RNA

<400> SEQUENCE: 20
agccggagcg gacgcccgtt ggg                                                    23
```

SCREENING METHOD FOR TELOMERASE REVERSE TRANSCRIPTASE (TERT) PHOSPHORYLATION INHIBITORS

TECHNICAL FIELD

The present invention relates to a method for screening for a telomerase reverse transcriptase (TERT) phosphorylation inhibitor, and the like.

BACKGROUND ART

A telomere is a repetitive sequence of a chromosome end, and protects an intact chromosome. Meanwhile, it is known that a telomere reduces the continuous rounds of cell division gradually, and very shortened telomere induces aging and apoptosis.

As a catalytic subunit of telomerase, which is an enzyme which elongates a telomere and maintains its structure, although telomerase reverse transcriptase (TERT) is expressed at a high level in malignant cells, TERT is expressed at a very low level in normal cells.

Although telomerase activity for maintaining telomere structure is known as an activity of TERT, it has been reported recently that TERT also has RNA-dependent RNA polymerase (RdRP) activity (Non Patent Literature 1).

RNA-dependent RNA polymerase is an enzyme which uses RNA as a template and synthesizes opposite RNA, and double strand RNA is produced by forming these RNA strands into a pair.

The RdRP activity of TERT exhibits enzyme activity by using non-protein-encoding RNA such as the RNA component of mitochondrial RNA processing endoribonuclease (RMRP) as a template.

It is also known that TERT forms a TBN complex with helicase BRG1 and nucleostemin (NS), and is involved in the function maintenance of cancer stem cells (Non Patent Document 2).

Moreover, it is known that an increase in M phase-specific RdRP activity of TERT is involved in the function maintenance of cancer stem cells (Non Patent Documents 3 and 4).

PRIOR ART DOCUMENT(S)

Non Patent Document(s)

Non Patent Document 1: Cancer Sci 106 (2015) 1486-1492
Non Patent Document 2: Proc Natl Acad Sci USA 108 (2011) 20388-20393
Non Patent Document 3: Mol Cell Biol 34 (2014) 1576-1593
Non Patent Document 4: Mol Cell Biol 36 (2016) 1248-1259

DISCLOSURE OF INVENTION

Problem to be Solved by the Invention

It is considered that since the RdRP activity of TERT is involved in the function maintenance of cancer stem cells, noticing the RdRP activity of TERT leads to the creation of an anticancer drug by a new mechanism.

However, the RdRP activity of TERT is not widely known even now, and a mechanism when TERT does not exhibit original telomerase activity but RdRP activity is unknown.

Therefore, clarifying the mechanism of the RdRP activity of TERT can be a target molecular basis for treating cancer.

Means for Solving Problem

The present inventors have examined earnestly and consequently found that the phosphorylation of TERT triggers the RdRP activity of TERT.

The present invention is based on such knowledge.

The present invention is as follows.

(1)

A method for screening for a telomerase reverse transcriptase (TERT) phosphorylation inhibitor using TERT or a fragment thereof, and a TERT kinase.

(2)

The screening method according to (1), wherein a phosphorylation site is any amino acid residue of T249, S255, T1088 and S1095 in the telomerase reverse transcriptase (TERT) or a fragment thereof.

(3)

The screening method according to (1), wherein a phosphorylation site is T249 in the telomerase reverse transcriptase (TERT) or a fragment thereof.

(4)

The screening method according to any one of (1) to (3), wherein the telomerase reverse transcriptase (TERT) kinase is cyclin-dependent kinase 1 (CDK1).

(5)

The screening method according to any one of (1) to (4), wherein the fragment of telomerase reverse transcriptase (TERT) has an amino acid sequence comprising any amino acid residue of T249, S255, T1088 and S1095.

(6)

A method for predicting prognosis of cancer treatment, wherein the prognosis is estimated as poor when any amino acid residue of T249, S255, T1088 and S1095 of telomerase reverse transcriptase (TERT) is phosphorylated.

(7)

A telomerase reverse transcriptase (TERT) or a fragment thereof, wherein T249 in the telomerase reverse transcriptase (TERT) is replaced with alanine or glutamic acid.

(8)

A telomerase reverse transcriptase (TERT) or a fragment thereof, wherein any amino acid residue of T249, S255, T1088 and S1095 in the telomerase reverse transcriptase (TERT) or a fragment thereof is phosphorylated.

(9)

An anti-telomerase reverse transcriptase (TERT) antibody that recognizes any amino acid sequence of SEQ ID NOs: 1 to 4.

Effect of the Invention

According to the present invention, a method for screening for a telomerase reverse transcriptase (TERT) phosphorylation inhibitor can be provided.

BRIEF DESCRIPTION OF DRAWINGS

FIG. 1 First, HeLa cells or 293T cells were synchronized in the M phase, and human TERT (hTERT) was immunoprecipitated with a 10E9-2 antibody (MBL) and purified. The preparation was analyzed by mass spectrometry, and two phosphorylated peptides were identified. The identified peptides were 241-GAAPEPERTPVGQGSWAHPGR-261 (SEQ ID NO: 18) and 1087-VTYVPLLGSLR-1097 (SEQ ID NO: 19), and these peptides had four sites which can be phosphorylated (shown underlined). Respective antibodies specifically recognizing phosphorylation sites were produced. Analysis was performed by dephosphorylation treatment with λ phosphatase (FIG. 1A) and the expression suppression of hTERT by siRNA (FIG. 1B). Consequently, since the disappearance of phosphorylation-specific signals were observed with the phosphorylated T249-recognizing antibody (Anti-hTERT pT249), the phosphorylation of T249 was confirmed.

FIG. 2 It was attempted to identify the upstream kinase involved in the phosphorylation of hTERT T249. Since the T249 site has a (S/T) P motif described in a previous paper, CDK1, Aurora B kinase, p38MAP kinase and the like were presumed and used to confirm whether the phosphorylation of hTERT T249 was maintained using siRNAs corresponding to respective kinases. Consequently, since the disappearance of the signal of hTERT pT249 was observed in cells treated with siRNA corresponding to CDK1, it was confirmed that CDK1 was essential for the phosphorylation of hTERT T249 (FIG. 2A). Moreover, it was confirmed that the RdRP activity of hTERT was also inhibited in cells treated with siRNA corresponding to CDK1 (FIG. 2B).

FIG. 4 hTERT in which T249, which was only one amino acid, was mutated was produced to confirm whether the phosphorylation of hTERT T249 is important for the function maintenance of cancer cells, and the influence on the proliferation of cancer cells was confirmed. A T249A mutant is a mutant in which phosphorylation does not occur by replacing the T with A and which dominantly and negatively suppresses the RdRP activity of hTERT existing internally (A mutant). Meanwhile, a T249E mutant is a mutant imitating the same site being phosphorylated constantly by replacing the T with E (E mutant).

FIG. 6 Since it was found that the phosphorylation of T249 with CDK1 is essential for the proliferation of cancer cells, it was investigated using human cancer patient specimens whether the convalescence and relapse of cancer patients were involved in whether T249 phosphorylation was detected or not. It was examined thereby whether T249 phosphorylation could be considered to be a therapeutic target. First, 102 examples of cancer tissues of liver cancer patient specimens were immunostained with anti-hTERT pT249 and classified into examples wherein hTERT T249 phosphorylation (pT249) detection was negative (an example is shown as FIG. 6A) and examples wherein pT249 detection was positive (an example is shown as FIG. 6B) (an example was determined to be positive when pT249 positive cells covered 10% or more of one field of view).

FIG. 9 It was confirmed that while RdRP activity was remarkably suppressed also in the T249A-CRISPR cells, the telomerase activity was not affected. That is, T249 phosphorylation was necessary for RdRP activity also in the T249A-CRISPR cells. In the T249A-CRISPR cells, while it was observed that tumorigenicity was remarkably suppressed, telomere length was maintained longer than in the control. It can be said from this that TERT in which T249 in TERT is replaced with alanine (T249A mutant) is a "cancer-suppressing and antiaging (long life) enzyme."

BEST MODE FOR CARRYING OUT THE INVENTION

Figure 3:
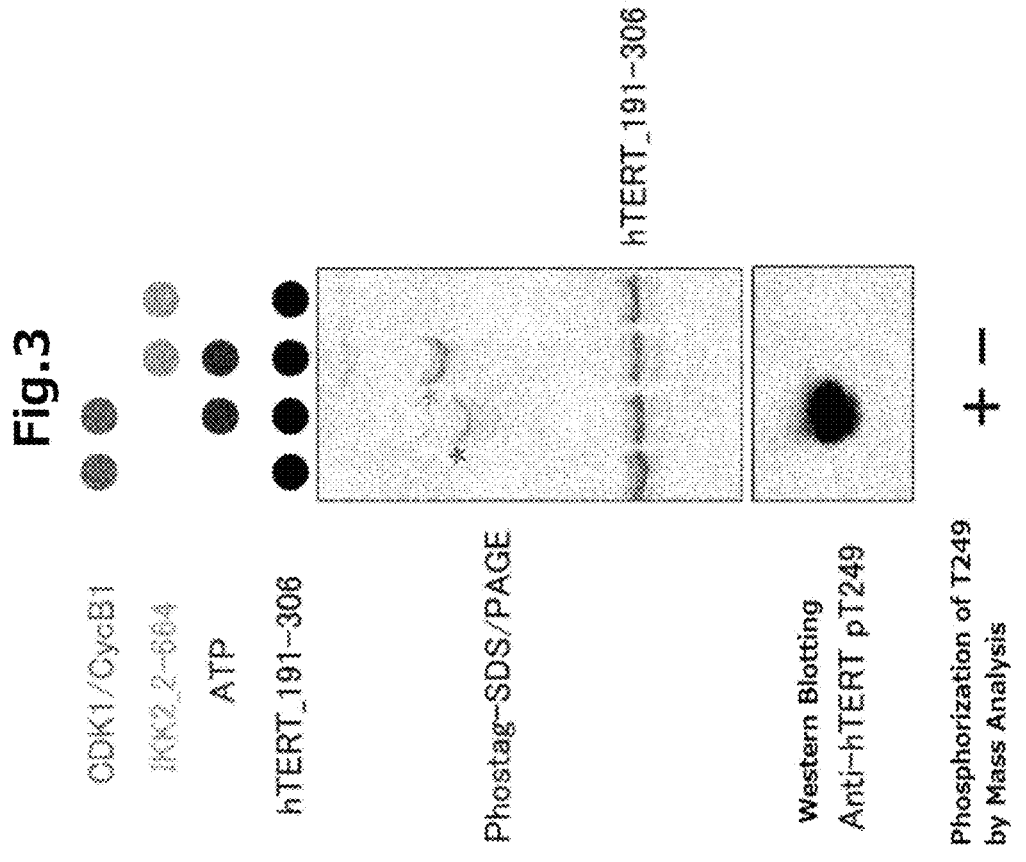
FIG. 3 It was confirmed in vitro whether hTERT T249 was phosphorylated (pT249) with CDK1. When bands which were considered to be phosphorylated by reacting hTERT_191-306 expressed in a cell-free synthesis system and purified with commercially available CDK1 or IKK2 which was a negative control, (shown with asterisk) were collected and analyzed by mass spectrometry, pT249 was detected from only a sample treated with CDK1. Meanwhile, pS206, pS274, pT283 and the like were detected from a sample treated with IKK2. When the same samples were subjected to Western blotting using Anti-hTERT pT249, a signal was detected from only the sample treated with CDK1. From these experiments, it was confirmed that CDK1 phosphorylates the amino acid residue T at position 249 in hTERT, and Anti-hTERT pT249 recognizes the phosphorylated amino acid residue T at position 249 in hTERT.

The present invention is a method for screening for a telomerase reverse transcriptase (TERT) phosphorylation inhibitor.

Telomerase reverse transcriptase (TERT) or a fragment thereof, and telomerase reverse transcriptase (TERT) kinase are used in the screening method.

TERT or a fragment thereof is a substrate for a TERT kinase, and has phosphorylation sites by TERT kinase.

As long as the phosphorylation sites are sites to be phosphorylated by kinase, the phosphorylation sites are not particularly limited. Examples of the phosphorylation sites however include a serine residue and a threonine residue.

The screening method of the present invention is a method for searching for a substance which inhibits TERT phosphorylation using the phosphorylation of the sites in TERT or a fragment thereof to be phosphorylated by the TERT kinase as an index.

The substance selected by the screening method of the present invention is a phosphorylation inhibitor which inhibits (blocks) the phosphorylation of TERT or a fragment thereof by the TERT kinase.

Since the TERT phosphorylation inhibitor selected by the screening method of the present invention inhibits the phosphorylation of TERT, which is the starting point of a mechanism for expressing the RdRP activity of TERT, the phosphorylation inhibitor inhibits the RdRP activity of TERT.

Since the RdRP activity of TERT is involved in the function maintenance of cancer stem cells, the TERT phosphorylation inhibitor inhibits the RdRP activity of TERT and then disables cancer stem cells from maintaining the function. It is also considered that the TERT phosphorylation correlates with the malignancy and the relapse of cancer.

Therefore, the TERT phosphorylation inhibitor selected by the screening method of the present invention may be able to be used as an anticancer drug by a new mechanism.

As long as the TERT phosphorylation inhibitor is a substance which reduces or eliminates the activity of the TERT kinase, the TERT phosphorylation inhibitor is not particularly limited. Examples of the TERT phosphorylation inhibitor include proteins such as antibodies, peptides, peptide mimetics, nucleic acids, carbohydrates, lipids, and low-molecular compounds.

In the screening method of the present invention, at least TERT or a fragment thereof, and a TERT kinase are used.

The screening for a substance that is a TERT phosphorylation inhibitor can be performed by confirming that the phosphorylation of TERT or a fragment thereof by a TERT kinase is inhibited.

The mode of inhibition is not particularly limited, or a method for confirming that the phosphorylation of TERT or a fragment thereof is inhibited is not particularly limited, either. The screening for TERT phosphorylation inhibitor can be performed by searching for a substance which suppresses or eliminates the phosphorylation as to a positive control, to which the test substance is not added.

The derivation of TERT or a fragment thereof is not particularly limited. Although TERT or a fragment thereof may be derived from an animal such as a rodent such as a rat or a mouse; a simian; a dog; a rabbit or a guinea pig known as a model animal, it is preferable to use telomerase reverse transcriptase (TERT) or a fragment thereof derived from a human.

TERT having a full length may be used as TERT or a fragment thereof. If a peptide has amino acid residues which are phosphorylation sites phosphorylated by kinase or the like and are the starting point of the cascade of RdRP activation, the peptide having an amino acid sequence which is a fragment of TERT can however be used as a substrate for the TERT kinase.

Examples of the phosphorylation sites of TERT include any amino acid residue of T249, S255, T1088 and S1095, and it is preferable that a phosphorylation site be T249.

T means a threonine residue, and S means serine residue as a phosphorylation site.

Although "249" in T249 means the amino acid residue at position 249 as counted from the N-terminus, T249 means the threonine at position 249 in TERT having an amino acid sequence (SEQ ID NO: 17) well-known as NP_937983 (https://www.ncbi.nlm.nih.gov/protein/NP_937983.2) or Uniprot ID O14746-1 (http://www.uniprot.org/uniprot/O14746).

A TERT on the here, T249 is preferably phosphorylated in the screening method of the present invention. When other than a TERT known as the above-mentioned NP_937983 or Uniprot ID O14746-1 is used as a fragment thereof on TERT, the phosphorylation site does not, however, mean the 249th threonine from N-terminus strictly.

That is, although it is one aspect to use a TERT having T249 in the screening method of the present invention, the TERT does not have an amino acid sequence known as NP_937983 or Uniprot ID O14746-1 essentially. A TERT derivative containing an amino acid sequence in which one or several dozen, preferably one or several, 1 to 10, 1 to 9, 1 to 8, 1 to 7, 1 to 6, 1 to 5, 1 to 4, 1 to 3, or 1 or 2 amino acids were add, replaced or deleted in the amino acid sequence of TERT known as NP_937983, or Uniprot ID O14746-1, and having the amino acid sequence having the phosphorylation capacity of TERT kinase and known as NP_937983 or Uniprot ID O14746-1 may be used, and telomerase reverse transcriptases identified as other TERTs may be used.

As long as the TERT derivative has the phosphorylation capacity of TERT kinase, the TERT derivative having an amino acid sequence with 70% or more, 80% or more, 90% or more, 95% or more, 96% or more, 97% or more, 98% or more, or 99% or more sequence identity with the amino acid sequence known as the NP_937983 or Uniprot ID O14746-1 as TERT may be used.

When these derivatives or the like are used, T249 means a threonine residue corresponding to T249 in the most highly homologous sequence with these derivatives aligned with the amino acid sequence known as the NP_937983 or Uniprot ID O14746-1. Preferably, threonine residues in an S/TP phosphorylation motif in the amino acid sequences of these derivatives may be used as phosphorylation sites corresponding to T249 in the amino acid sequence known as NP_937983 or Uniprot ID O14746-1.

As long as the fragment of telomerase reverse transcriptase (TERT) has amino acid residues corresponding to phosphorylation sites to be phosphorylated by TERT kinase, the fragment is not particularly limited.

As long as the fragment of TERT, for example, has amino acid residues corresponding to the phosphorylation sites, the fragment is not particularly limited. Examples of the fragment however include a fragment having a partial amino acid sequence of TERT with any amino acid residue of T249, S255, T1088 and S1095. For example, an amino acid sequence comprising the 191st position to the 306th position of human TERT is preferably used.

The fragment of TERT is preferably a fragment containing T249, and examples of the fragment include a fragment having an amino acid sequence comprising 10 amino acid residues such as the amino acid sequence set forth in SEQ ID NO: 1.

Examples of the fragment of TERT include a fragment located in a middle of chain length between a fragment having an amino acid sequence from the 245th position, which is the N-terminus of an amino acid sequence set forth in SEQ ID NO: 1, to the 254th position of TERT and a fragment having an amino acid sequence from the 191st position to the 306th position of TERT.

Specifically, a partial fragment of TERT may be a fragment comprising at least 3 amino acid residues including a phosphorylation site, and examples of the fragment include a fragment of TERT having an amino acid sequence wherein the N-terminus is selected from amino acid residues from the 191st position to the 245th position, and the C-terminus is selected from amino acid residues from the 254th position to the 306th position.

As long as TERT kinase is a kinase which perform the phosphorylation of TERT, which results in the RdRP activity of TERT, the TERT kinase is not particularly limited. However, CDK1 can be preferably used.

The derivation of the CDK1 is also not particularly limited. Although the CDK1 may be derived from an animal such as a rodent such as a rat or a mouse; a simian; a dog; a rabbit or a guinea pig known as a model animal, it is preferable to use CDK1 derived from a human.

A CDK1 having a full length may be used as CDK1. As long as a CDK1 has kinase activity, the CDK1 may however be a peptide having an amino acid sequence which is a fragment of CDK1.

In the screening method of the present invention, reagents used other than telomerase reverse transcriptase (TERT) or a fragment thereof, and telomerase reverse transcriptase (TERT) kinase may be used in a system used for a usual kinase assay, and reagents for performing a conventionally well-known phosphorylation test of the assay system are used. A kit containing at least telomerase reverse transcriptase (TERT) or a fragment thereof, and telomerase reverse transcriptase (TERT) kinase may be prepared, and the kit may contain the above-mentioned reagents.

The screening method of the present invention may be performed in a cell system, or may be performed in a cell-free system.

Telomerase reverse transcriptase (TERT) or a fragment thereof, and telomerase reverse transcriptase (TERT) kinase and the like used in the screening method of the present invention and produced by a conventionally well-known method may be used.

For example, a protein/peptide expressed in cells may be purified by a conventionally well-known method, and a protein/peptide may be expressed in cells, and may be used in a cell system as it is, and a protein/peptide expressed in

*Escherichia coli* or the like with genetic engineering techniques combined and purified may be used.

The present invention may be performed using M phase accumulation cells, and a method for accumulating the cells in the M phase can be performed according to a well-known method.

Although the cells are not particularly limited, it is preferable to use a cancer cell line derived from a cancer tissue.

Examples of the cancer cell line include, but are not particularly limited to, a 293T cell, a HeLa cell, PEO1 (ATCC), PEO14 (ATCC), ES-2 (ATCC), Alex, HLE, a HuH7 cell and U87MG.

Examples of a method for confirming the phosphorylation of TERT or a fragment thereof include, but are not particularly limited to, methods for detecting the phosphorylation immunologically such as Western blotting, tissue immunostaining, cell immunostaining and dot blotting. The phosphorylation may also be detected by a fluorescent antibody method, an Enzyme-Linked ImmunoSorbent Assay (ELISA), a radioactive substance-labeled immuno-antibody method (RIA), sandwich ELISA or the like.

In the screening method of the present invention, it may be confirmed whether phosphorylation occurs by a method for immunoprecipitating TERT or a fragment thereof for confirmation by Western blotting, or mass spectrometry.

When the phosphorylation of TERT or a fragment thereof is confirmed, it is preferable to use an antibody which recognizes the amino acid sequence of TERT or a fragment thereof having such a phosphorylated amino acid residue.

The antibody is an amino acid sequence containing an amino acid residue to be phosphorylated, and the antibody can be produced by a conventionally well-known method using a peptide in which the amino acid residue is phosphorylated as an antigen.

It is preferable to use a peptide having a partial amino acid sequence of TERT which has any amino acid residue of T249, S255, T1088 and S1095 as such an antigen and in which the amino acid residue is phosphorylated as an antigen.

When the antibody is obtained, for example, an adjuvant may be used together, or an antigen in which immunity is activated by binding a peptide in which C is connected with the 5'-terminus of an amino acid sequence derived from TERT which is an antigen to KLH may be used.

Since an animal producing the antibody is not particularly limited, the derivation of the antibody which recognizes the amino acid sequence of TERT having the phosphorylated amino acid residue is not particularly limited, either.

The antibody in the present invention is an antibody which is derived from TERT and recognizes the phosphorylated amino acid sequence, and the phosphorylation causes the RdRP activity of TERT.

The antibody in the present invention can recognize phosphorylated TERT.

The antibody in the present invention is specifically preferably an antibody which recognizes any of the amino acid sequences set forth in SEQ ID NOs: 1 to 4 and derived from TERT. The antibody in the present invention is also an antibody obtained using a peptide in which a peptide having an amino acid sequence set forth in SEQ ID NOs: 5 to 8 and derived from TERT is bound to KLH as an antigen.

The antibody in the present invention is an antibody which is derived from TERT and recognizes a phosphorylated amino acid sequence, and may be any of antibodies which recognize the amino acid sequences set forth in SEQ ID NOs: 1 to 4 and derived from TERT and are obtained using peptides in which peptides having amino acid sequences set forth in SEQ ID NOs: 5 to 8 and derived from TERT are bound to KLH as antigens, respectively.

As long as the antibody in the present invention is an antibody which recognizes any of the amino acid sequences set forth in SEQ ID NOs: 1 to 4 and derived from TERT, the antibody may be obtained using a peptide having an amino acid sequence having a longer chain length than the amino acid sequences set forth in SEQ ID NOs: 1 to 4 and derived from TERT as an antigen.

The antibody in the present invention may be a polyclonal antibody, or may be a monoclonal antibody, and the monoclonal antibody can also be produced by a method well-known to those skilled in the art. The antibody in the present invention may be a chimeric antibody, or may be a humanized antibody or a human antibody.

The antigen-binding fragments of antibodies can also be provided in the present invention.

Examples of the antigen-binding fragments include bispecific antibodies such as a diabody type, a scDb type, a tandem scFv type and a leucine zipper type besides Fab, which comprises of VL, VH, CL and CH1 regions; F(ab')2, in which two Fab are connected in hinge regions by a disulfide bond; Fv, which comprises VL and VH; and scFv, in which VL and VH are connected by an artificial polypeptide linker and which is a single chain antibody.

In the present invention, it is confirmed that when a specific amino acid residue is phosphorylated in human TERT, prognosis is poor.

Therefore, poor prognosis in cancer treatment can be confirmed by confirming whether such an amino acid residue is phosphorylated in humans. That is, phosphorylation in the specific amino acid residue in TERT can be used as a poor prognostic predictive factor in cancer treatment.

In the present invention, for example, lesional tissue is obtained from a cancer patient and stained by immunological techniques. It can be determined that prognosis in cancer treatment is poor by confirming that staining positive cells exist, for example, at 5% or more, 10% or more, or 20% or more of one field of view.

The present invention also provides a method for predicting prognosis of cancer treatment, wherein when any amino acid residue of T249, S255, T1088 and S1095 of telomerase reverse transcriptase (TERT) is phosphorylated, it is estimated that prognosis is poor. The method for predicting prognosis in the present invention may be used as a method for diagnostic assistance.

A method used in the method for confirming the phosphorylation of TERT or a fragment thereof in the screening method of the present invention can be used to confirm that any amino acid residue of T249, S255, T1088 and S1095 of telomerase reverse transcriptase (TERT) is phosphorylated in the method for predicting prognosis of cancer treatment of the present invention.

TERT or a fragment thereof wherein any amino acid residue of T249, S255, T1088 and S1095 is phosphorylated in TERT can also be used as a detection marker.

In the present invention, it is confirmed that the RdRP activity of TERT results from the phosphorylation of TERT by TERT kinase.

Telomerase reverse transcriptase (TERT) wherein the telomerase reverse transcriptase (TERT) is a mutant of TERT obtained in the process, and T249 in the telomerase reverse transcriptase (TERT) is replaced with alanine or glutamic acid can be represented by a T249A mutant (alanine mutant) or a T249E mutant (glutamic acid mutant).

The alanine mutant has the effect of suppressing cancer cell proliferation, and the glutamic acid mutant has the effect of increasing cancer cell proliferation.

While the alanine mutant suppresses essential activity for cancer cell proliferation (RdRP activity) dominantly and negatively, telomere elongation enzyme activity is maintained as it is. Here, since it is well-known that the telomere elongation enzyme "acts on antiaging," the alanine mutant can also be recognized as a cancer suppressing and antiaging enzyme.

Therefore, the alanine mutant is provided as TERT having cancer suppressing and antiaging effects by the present invention.

The T249A mutant (alanine mutant) or the T249E mutant (glutamic-acid mutant) in the present invention may be a peptide wherein the peptide has an amino acid sequence set forth in SEQ ID NO: 17, and threonine at the 249th position is mutated to alanine or glutamic acid, or may be a peptide having an amino acid sequence with 70% or more, 80% or more, 90% or more, 95% or more, 96% or more, 97% or more, 98% or more, or 99% or more sequence identity with the amino acid sequence set forth in SEQ ID NO: 17 as long as the amino acid residue corresponding to threonine at the 249th position (preferably, the threonine residue of a S/TP phosphorylation motif) is replaced with alanine or glutamic acid.

The T249A mutant (alanine mutant) and the T249E mutant (glutamic acid mutant) in the present invention may be a peptide having an amino acid sequence wherein one or several dozen, preferably one or several, 1 to 10, 1 to 9, 1 to 8, 1 to 7, 1 to 6, 1 to 5, 1 to 4, 1 to 3, or 1 or 2 amino acids are added, replaced or deleted in the amino acid sequence set forth in SEQ ID NO: 17 as long as the amino acid residue corresponding to threonine at the 249th position (preferably, the threonine residue of a S/TP phosphorylation motif) is replaced with alanine or glutamic acid.

The T249A mutant (alanine mutant) or the T249E mutant (glutamic acid mutant) may be a fragment of the T249A mutant (alanine mutant) or the T249E mutant (glutamic acid mutant) as long as the fragment has the above-mentioned activity.

In the present invention, telomerase reverse transcriptase (TERT) wherein T249 in TERT is phosphorylated is also provided.

TERT wherein T249 was phosphorylated can be used as a therapeutic target.

TERT in which T249 in TERT is phosphorylated in the present invention may be a peptide wherein the peptide has an amino acid sequence set forth in SEQ ID NO: 17, and threonine at the 249th position is phosphorylated, or may be a peptide having an amino acid sequence with 70% or more, 80% or more, 90% or more, 95% or more, 96% or more, 97% or more, 98% or more, or 99% or more sequence identity with the amino acid sequence set forth in SEQ ID NO: 17 as long as the amino acid residue corresponding to threonine at the 249th position (preferably, the threonine residue of a S/TP phosphorylation motif) is phosphorylated.

TERT wherein T249 in TERT is phosphorylated in the present invention may be a peptide having an amino acid sequence wherein one or several dozen, preferably one or several, 1 to 10, 1 to 9, 1 to 8, 1 to 7, 1 to 6, 1 to 5, 1 to 4, 1 to 3, or 1 or 2 amino acids are added, replaced or deleted in the amino acid sequence set forth in SEQ ID NO: 17 as long as the amino acid residue corresponding to threonine at the 249th position (preferably, the threonine residue of a S/TP phosphorylation motif) is replaced with alanine or glutamic acid.

As long as threonine at the 249th position is phosphory-lated, TERT may be a fragment of TERT in which T249 in TERT is phosphorylated.

EXAMPLES

Although the present invention will be described by the Example and the Reference Examples more specifically hereinafter, the present invention is not limited to these.
Production of Anti-hTERT pT249 Antibody
1. Peptide Synthesis Samples obtained after "(2) immunoprecipitation" in the following "detection of phosphorylated hTERT" were used to be analyzed by mass spectrometry, and two phosphory-lated peptides were identified. Since four points which may be phosphorylated existed in the amino acid sequences of the identified peptides, the following four amino acid sequences were selected around the amino acid residues which may be phosphorylated. pT and pS mean phospho-rylated threonine and phosphorylated serine.

|  |  |
|---|---|
| EPERpTPVGQG | (SEQ ID NO: 1) |
| VGQGpSWAHPG | (SEQ ID NO: 2) |
| RHRVpTYVPLL | (SEQ ID NO: 3) |
| PLLGpSLRTAQ | (SEQ ID NO: 4) |

Oligopeptides having amino acid sequences of SEQ ID NOs: 5 to 8 were synthesized by a usual method. The molecular weight of the object was confirmed by mass spectrometry, and the oligopeptides were purified to a purity >90% by HPLC purification.

| hTERT T249 | |
|---|---|
| CEPERpTPVGQG | (SEQ ID NO: 5) |
| hTERT S255 | |
| CVGQGpSWAHPG | (SEQ ID NO: 6) |
| hTERT T1088 | |
| CRHRVpTYVPLL | (SEQ ID NO: 7) |
| hTERT S1095 | |
| CPLLGpSLRTAQ | (SEQ ID NO: 8) |

All the oligopeptides have partial sequences in hTERT. All the amino acid sequences which the oligopeptides have are amino acid sequences wherein threonine or serine con-sidered to be phosphorylation sites is phosphorylated, and C (cysteine, Cys) is connected with the N-terminus of each of the amino acid sequences.
2. KLH Binding First, 8 mg of KLH and 5 mg of the crosslinking agent EMCS were bound by a bisimide ester method through an amino group, and gel filtration purification was then per-formed. Next, the KLH-EMCS complex and 4 mg of a peptide were bound through the SH group of Cys, and the immunogen was secured.
3. Production of Rabbit Antiserum Antigen sensitization was performed on Day 0, 14, 28, and 49 a total of 4 times. The phosphorylated peptide was used in an amount of 100 µg per once. The sensitized sites in all the steps is intradermal, and an FCA (freund complete adjuvant) was used for an adjuvant. Partial exsanguination was performed on Day 42, and the phosphorylated peptide was subjected to the ELISA measurement and Western blotting.
4. Purification of Specific Antibody (Affinity Purification)

Figures 1A, 1B:
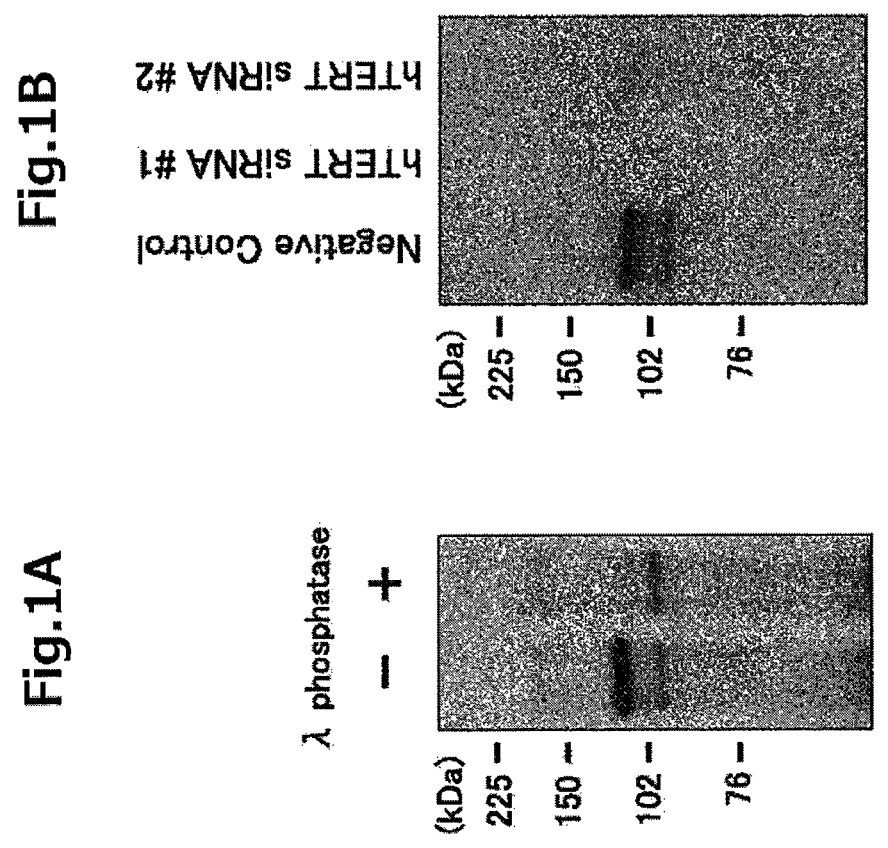

Purification columns were manufactured using 4 to 5 mg of a phosphorylated peptide and a non-phosphorylated pep-tide. CNBr-activated sepharose 4B was used for a column carrier. The antiserum was passed through the phosphory-lated peptide column. The fraction adsorbing to the column was eluted, the eluted fraction was passed through the non-phosphorylated peptide column, and a non-phosphory-lated antibody were absorbed. The fraction passing the non-phosphorylated peptide column (phosphorylation spe-cific antibody) was collected. The collected passing fraction was subjected to ELISA using the phosphorylated peptide and the non-phosphorylated peptide, and the reactivity was confirmed to obtain anti-telomerase reverse transcriptase (TERT) antibodies which recognize the amino acid sequences of SEQ ID NOs: 1 to 4, respectively. An anti-TERT antibody which recognizes the amino acid sequence of EPERpTPVGQG (SEQ ID NO: 1) was defined as an anti-hTERT pT249 antibody.
Detection of Phosphorylated hTERT (Immunoprecipita-tion—Western Blotting)
(1) Preparation of M Phase Accumulation Cells First, $1\times10^6$ Hela cells (ATCC) cultured from the previous day were inoculated per 10-cm dish using DMEM medium (Wako) to which 10% inactivated fetal bovine serum (IFS), penicillin (100 U/mL) and streptomycin (100 µg/mL) were added as usual medium. The cells were cultured for 2 days, and the usual medium was then replaced with medium wherein thymidine (NACALAI TESQUE, final 2.5 mM) was further added to the usual medium, followed by culture. The cells were cultured for 24 hours, then washed 3 times with 10 mL of PBS (phosphate buffered saline) and cultured with the medium replaced with the usual medium. The cells were cultured for 6 hours and then cultured with the medium replaced with medium wherein nocodazole (Sigma, final 0.1 µg/mL) was further added to the usual medium. The cells were cultured for 14 hours and then collected.
(2) Immunoprecipitation The collected cells were washed with cooled PBS, $1\times10^7$ cells were suspended in 1 mL of a lysis buffer A (20 mM Tris-HCl (pH 7.4), 150 mM NaCl, 0.5% Nonidet P-40 (NP-40)), sonicated for 10 seconds and then centrifuged to collect the supernatant. Then, 40 µL of protein A agarose (Thermo Fisher Scientific, bed volume 20 µL) was added to the supernatant, and the mixture was rotated at 4° C. for 30 minutes, followed by preclearing. After centrifugation, the supernatant was collected, 40 µL of protein A agarose (bed volume 20 µL) and 10 µg of an anti-hTERT antibody (MBL M216-3) were added, and the mixture was rotated at 4° C. for 18 hours, resulting in immunoprecipitation. The agarose after the immunoprecipitation was washed 3 times with 1 mL of a lysis buffer A.
(3) λ-Phosphatase Treatment To 20 µL of agarose after immunoprecipitation and wash-ing were added 5 µL of λ-phosphatase (BioAcademia), 5 µL of 10×λ-phosphatase buffer (500 mM Tris-HCl (pH 7.6), 1 M NaCl, 20 mM dithiothreitol, 1 mM EDTA, 0.1% Bryj 35), 5 µL of 20 mM MnCl₂, and 15 µL of H₂O, followed by reaction at 30° C. for 30 minutes. FIG. 1A shows the results.

(4) Method for Preparing Protein Knockdown M Phase Accumulation Cells by siRNA

First, 1×10⁶ HeLa cells per 10-cm dish were inoculated using DMEM medium (Wako) to which 10% IFS was added as medium (8 mL), cultured for 16 to 18 hours and then transfected with siRNA.

The transfection was specifically performed by the following method.

1. To 1 mL Opti-MEM was added 20 µL of Lipofectamine 2000 (Invitrogen).

2. To 1 mL of Opti-MEM (Gibco) was added 330 pmol of siRNA.

3. Finally, 1 and 2 were mixed, and the mixture was left to stand at room temperature for 20 minutes and dropped into the 10-cm dish.

The medium was replaced with medium containing nocodazole (final 0.1 µg/mL) 48 hours after the transfection. The cells were cultured for 16 to 18 hours and then collected. FIGS. 1B and 2 show the results using these cells.

siRNAs shown in Table 1 were used.

TABLE 1

| hTERT siRNA#1 | sense strand | 5'-GUGUCUGUGCCCGGGAGAATT |
| | antisense strand | 5'-UUCUCCCGGGCACAGACACTT |
| hTERT siRNA#2 | sense strand | 5'-GCAUUGGAAUCAGACAGCATT |
| | antisense strand | 5'-UGCUGUCUGAUUCCAAUGCTT |
| CDK1 siRNA#1 | | Sigma Genosys SASI_Hs01_00044049 |
| CDK1 siRNA#2 | | Sigma Genosys SASI_Hs01_00044053 |
| CDK1 siRNA#3 | | Sigma Genosys SASI_Hs01_00056210 |
| NC siRNA | | Sigma Genosys Mission SIC_001 |

(5) Western Blotting

To the agarose after the immunoprecipitation were added 20 µL of a 2×SDS buffer (100 mM Tris-HCl (pH 6.8), 4% (w/v) SDS, 20% (v/v) glycerol, 2% (v/v) 2-mercaptoethanol, 0.01% (w/v) bromophenol blue). Denaturation was performed at 95° C. for 5 minutes, separation was then performed by SDS PAGE, and transference onto a nitrocellulose membrane was performed using a wet type transferring apparatus (GE Healthcare) (4° C., 18 hours). The membrane after the transference was blocked by a blocking buffer (TOYOBO NYPBR01) at room temperature for 1 hour, washed with a tris hydrochloric acid buffer containing 0.1% Tween 20 (TBST), reacted with the anti-hTERT pT249 antibody (1:1000 dilution) at room temperature for 1 hour, washed with TBST, further reacted with an anti-rabbit IgG-HRP antibody (GE Healthcare) at room temperature for 1 hour, washed with TBST, and then detected with an ECL reagent (Roche, Lumi Light Plus Western Blotting Substrate). TBST containing 2.5% bovine serum albumin (BSA) was used for an antibody diluent. FIGS. 1A, 1B and 2A show the results.

Method for Measuring IP-RdRP Activity

Measurement was performed in accordance with the method described in Mol Cell Biol 34: 1576-1593, 2014, Mol Cell Biol 36: 1248-1259, 2016. FIG. 2B shows the results.

In Vitro Kinase Assay Using hTERT 191-306

(1) Purification of hTERT (191-306)

The cDNA corresponding to the TERT191-306 amino acid site of hTERT[NP_937983 (https://www.ncbi.nlm. nih.gov/protein/NP_937983.2), or Uniprot ID O14746-1, (http://www.uniprot.org/uniprot/O14746)] is introduced into a pCR2.1-TOPO vector (Thermo Fisher Scientific), and a protein was expressed using a cell-free transcription and translation system [J Biochem. 2017 Nov. 1; 162(5):357-369]. Since the expressed protein was labeled with a poly-histidine Nil-tag at the N-terminus, Nil-tagged hTERT (191-306) was purified through an AKTA 10S system (GE Healthcare) using HisTrap columns (GE Healthcare). The columns were specifically washed with a concentration gradient buffer (50 mM Tris-HCl (pH 8.0), 1 M NaCl, 10 mM imidazole), and the protein was then eluted with an elution buffer (50 mM Tris-HCl (pH 8.0), 0.5M NaCl) having a concentration gradient of imidazole (from 10 to 500 mM). Imidazole was removed by dialysis. The poly-histidine Nil-tag at the N-terminus was removed with TEV protease using a TEV (Tobacco Etch virus) protease recognition site introduced artificially. This preparation was purified by ion exchange chromatography by a HiTrap SP column (GE Healthcare) and gel filtration by HiLoad 16/600 Superdex columns (GE Healthcare). The final concentration of the buffer containing the purified protein preparation was 25 mM Tris-HCl buffer (pH 7.0), 450 mM NaCl, and 0.25 mM TCEP [Tris (2-carboxyethyl) phosphine hydrochloride].

(2) Purification of IKK2 (2-664) Used as a Negative Control Instead of CDK1 of In Vitro Kinase Assay The cDNA corresponding to the 2 to 664 amino acid sites of IKK2 [Approved HGNC name, IKBKB; HGNC ID, 5960; UniProtKB ID, O14920] was introduced into a pDEST vector (Thermo Fisher Scientific). A protein was expressed using a Bac-to-Bac Baculovirus Expression System (Thermo Fisher Scientific). Poly-histidine affinity-labeled IKK2 (2-664) was expressed by infecting insect cells, Sf9 cells, with baculoviruses at a multiplicity of infection (MOI) of 1.0. The cells were collected within 48 hours after the infection, washed with PBS, and then freeze-preserved in liquid nitrogen. The IKK2 was purified in accordance with the below-mentioned paper. [J Biol Chem. 2013 Aug. 2; 288(31):22758-67.]

(3) In Vitro Kinase Assay

Kinase assay was performed at 37° C. for 2 hours using the purified hTERT (191-306) and CDK1-cyclin B (New England Biolabs).

The composition of a reaction liquid (40 µL) was as follows.

16 µL of hTERT 191-306 [0.33 µg/µL (25.86 µM)]

4 µL of 10×NE buffer (50 mM Tris-HCl (pH 7.5), 10 mM MgCl₂, 0.1 mM EDTA, 2 mM DTT, 0.01% Brij 35)

6 µL of CDK1-cyclin B (20 units/µL) or 6 µL of H₂O 12.5 µL of H₂O 1.5 µL of 125 mM ATP (Sigma, adenosine triphosphate) or 1.5 µL of H₂O To 10 µL of the sample after the reaction was added 10 µL of a 2.5×SDS sample buffer (140 mM Tris-HCl (pH 6.8), 5% (w/v) SDS, 250 mM 15% (v/v) glycerol, and 0.01% (w/v) bromophenol blue). The mixture was left to stand at 95° C. for 3 minutes to denature protein, and 10 µL of the mixture was separated by Phos-tag SDS-PAGE (http://www.wako-chem.co.jp/siyaku/product/life/phos-tag/pdf/Phos-tag4.pdf) (adjustment was performed so that the final concentration of hTERT was around 0.6 µg/lane). Staining was performed with Coomassie. FIG. 3 shows the results.

(4) Confirmation of Phosphorylation Site (Mass Spectrometry)

The asterisked band portions of the second lane and the third lane in FIG. 3 were cut out and subjected to digestive reaction at 37° C. for 20 hours with trypsin (Promega). The peptide preparation after the reaction was analyzed by LC-ESI-MS/MS.

(5) Western Blotting by Anti-hTERT pT249

First, 5 μL of hTERT 191-306 reacted with CDK1/CycB1 or IKK2_2-664 was separated by SDS PAGE and then transferred onto a nitrocellulose membrane using a wet type transferring apparatus. The phosphorylated hTERT was detected on the membrane after the transference with the anti-hTERT pT249 antibody by the above-mentioned method. FIG. 3 shows the results.

Proliferation Potency of Cells Expressing a Mutant and E Mutant

A mutant and E mutant plasmids were constructed using QuikChange II XL site-directed mutagenesis Kit (Agilent Technologies) according to a recommended protocol.

For the A mutant, the following primers were used:

5'-agccggagcgggcgcccgttggg-3' (SEQ ID NO: 13 Forward) and

5'-cccaacgggcgcccgctccggct-3' (SEQ ID NO: 14 Reverse)

For the E mutant, the following primers were used:

5'-tgagccggagcgggagcccgttgggcag-3' (SEQ ID NO: 15 Forward) and

5'-ctgcccaacgggctcccgctccggctca-3' (SEQ ID NO: 16 Reverse).

Figures 4A, 4B, 4C:
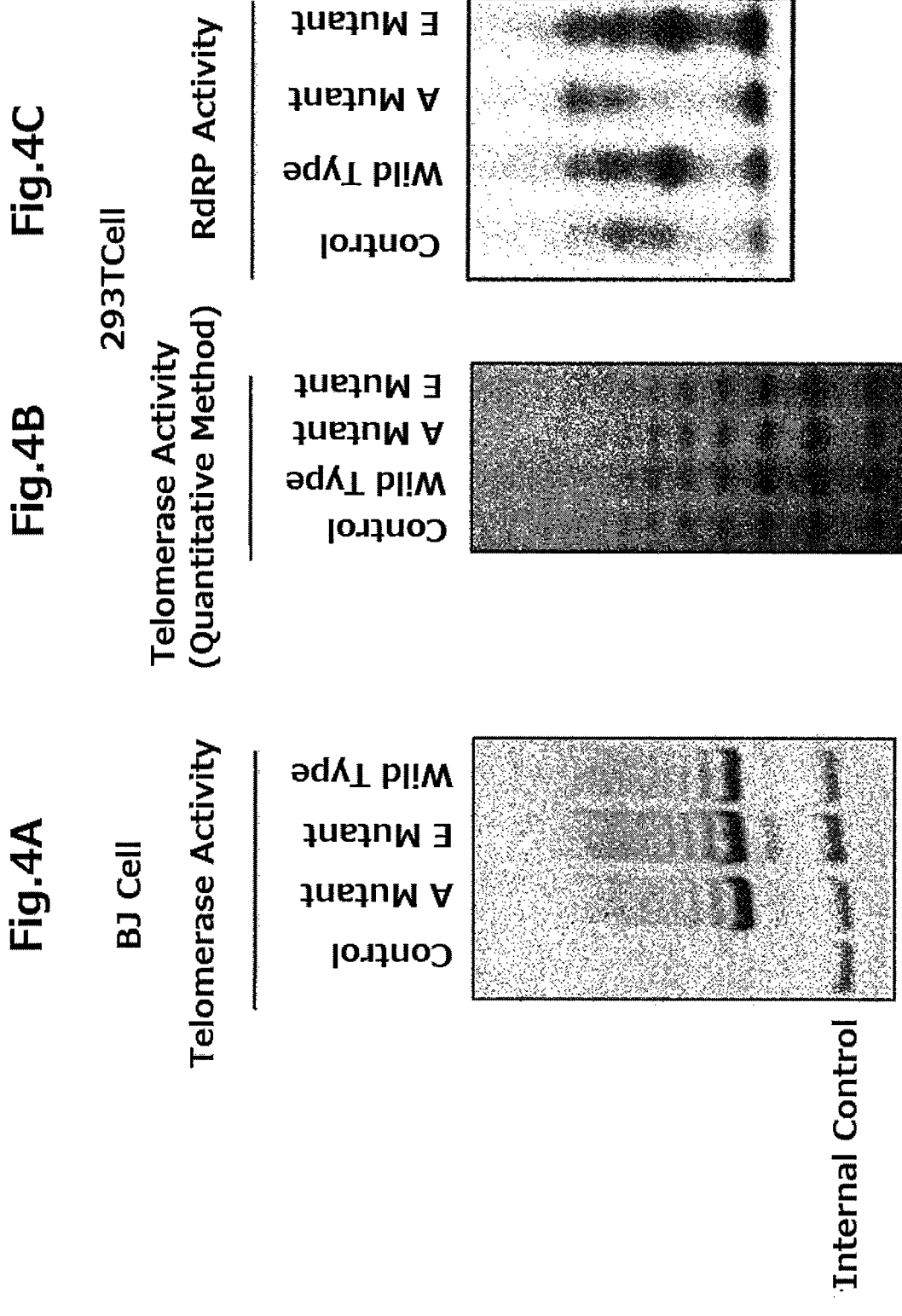
FIG. 4A shows the results obtained by introducing wild type hTERT, the A mutant and the E mutant into BJ cells not having telomerase activity and confirming telomerase activity. The telomerase activity of both hTERT mutants was confirmed. It could be confirmed that even though these mutants were introduced into 293T having telomerase activity, the telomerase activity (its increase and decrease were confirmed by quantitative method) was not affected (FIG. 4B). Meanwhile, influence on RdRP activity suppressed internal RdRP activity dominantly and negatively in the A mutant, and induced RdRP activity more strongly in the E mutant than in the wild type (FIG. 4C).

PCR was performed using the pBABE-puro-hTERT retroviral vector or the pNK-FLAG-z-hTERT expression vector as a template. The PCR product was treated with the restriction enzyme Dpn I at 37° C. for 1 hour, and transformed to XL-10-Gold ultracompetent cells. FIG. 4 shows the results obtained by testing the telomerase activity and the RdRP activity of the T249A mutant (A mutant) and the T249E mutant (E mutant).

Figure 5:
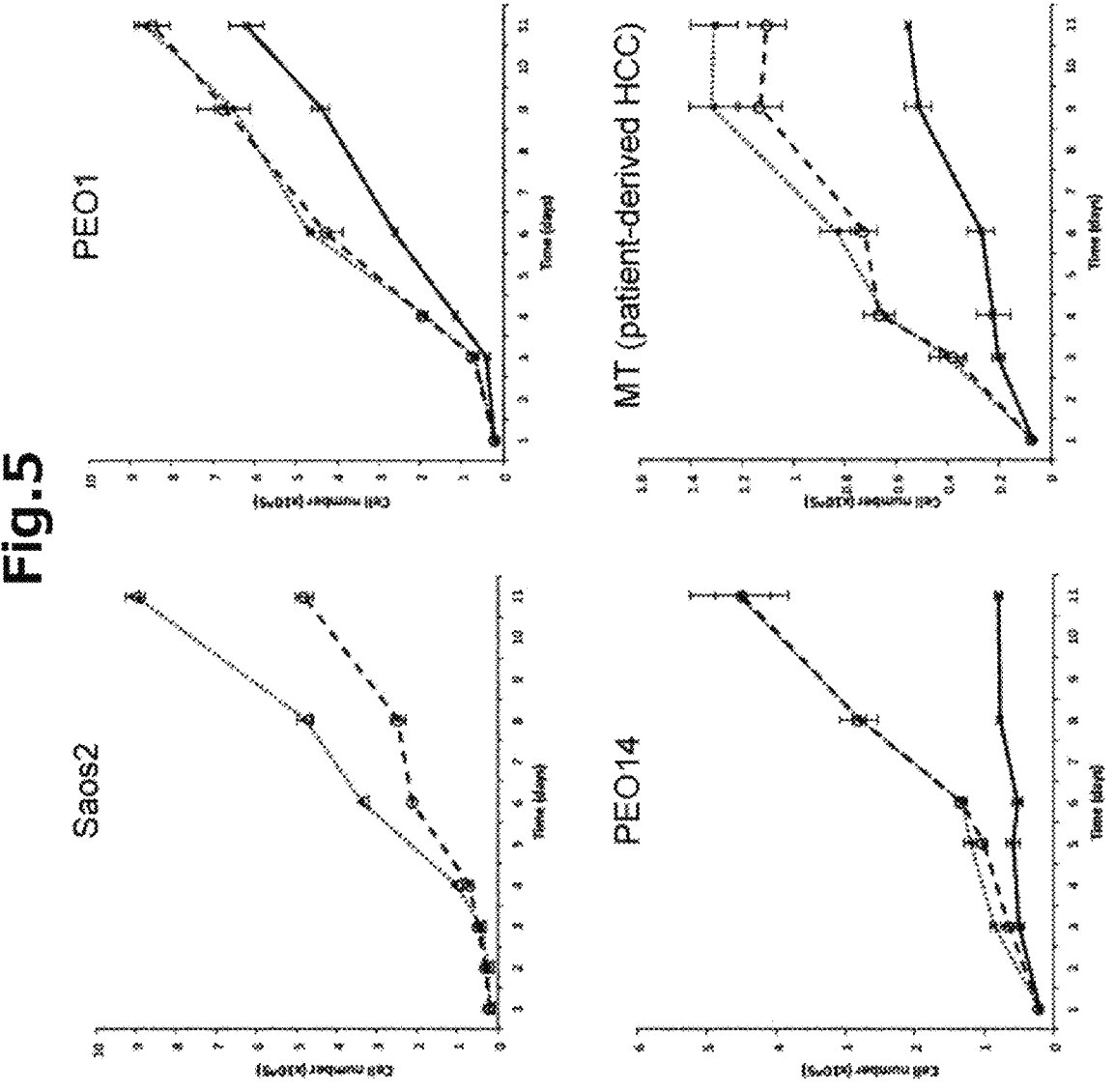
FIG. 5 When the E mutant was introduced into the Saos2 cell line, which was known not to express hTERT, the proliferation of cancer cells increased. In cancer cell lines (HCC-MT, PEO1 and PEO14), which were originally known to express hTERT, while the additional effect of cell proliferation increase in the E mutant itself was little, the effect of suppressing the proliferation of the cancer cells in the A mutant was observed very markedly. From this, it can be said that the phosphorylation of T249 itself is essential for the proliferation of cancer cells. A dashed line, a solid line and a dotted line in the figure show the cell growth curves of control cells, A mutant-introduced cells, and E mutant-introduced cells, respectively.

The T249A mutant and T249E mutant obtained by a retroviral vector (Takara, Retrovirus Packaging Kit Ampho) were introduced into each cell line of Saos2, HCC-MT, PEO1 and PEO14. The proliferation potency was confirmed by inoculating 20000 cells/well (only HCC-MT was 7000 cells/well) of each type of the transgenic cells on a 24-well plate, and measuring the number of cells over time. FIG. 5 shows the results.

DMEM medium (Wako) to which 10% IFS, penicillin (100 U/mL) and streptomycin (100 μg/mL) were added was used as the medium of Saos2 and HCC-MT.

RPMI-1640 medium (Sigma) to which 10% IFS, penicillin (100 U/mL), streptomycin (100 μg/mL) and sodium pyruvate (2 mM) were added was used as the medium of PEO1 and PEO14.

Figures 6A, 6B, 6C, 6D:
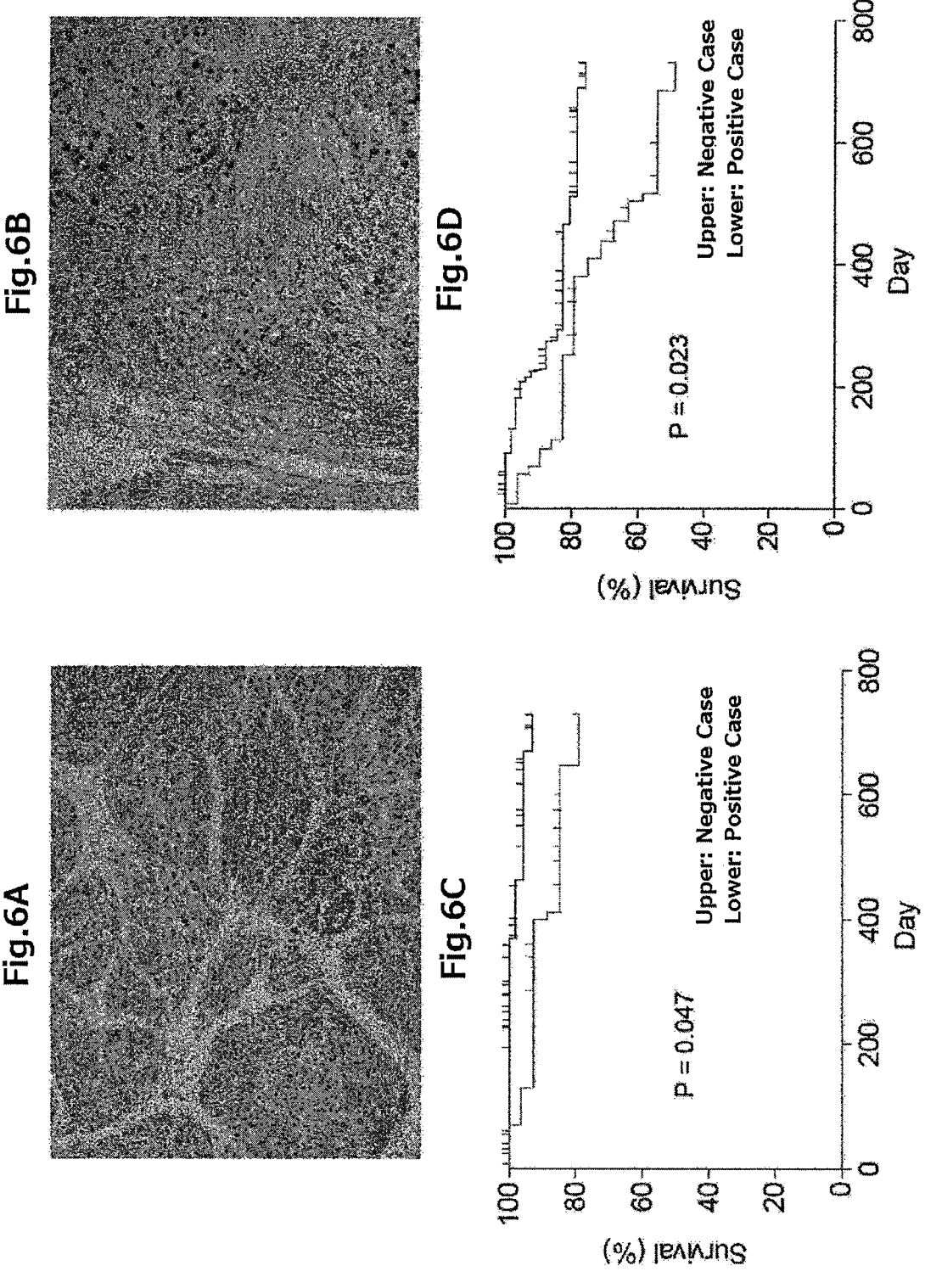
FIG. 6C shows the total survival period.
FIG. 6D shows the relapse-free survival period. It was found that both total survival period (FIG. 6C, p value<0.05) and relapse-free survival period (FIG. 6D, p value<0.05) were significantly short in the staining positive examples. It was confirmed that T249 phosphorylation itself corelated with the malignancy and the relapse of cancer, and was a target molecular basis for treating cancer.
Figures 7A, 7B, 7C, 7D:
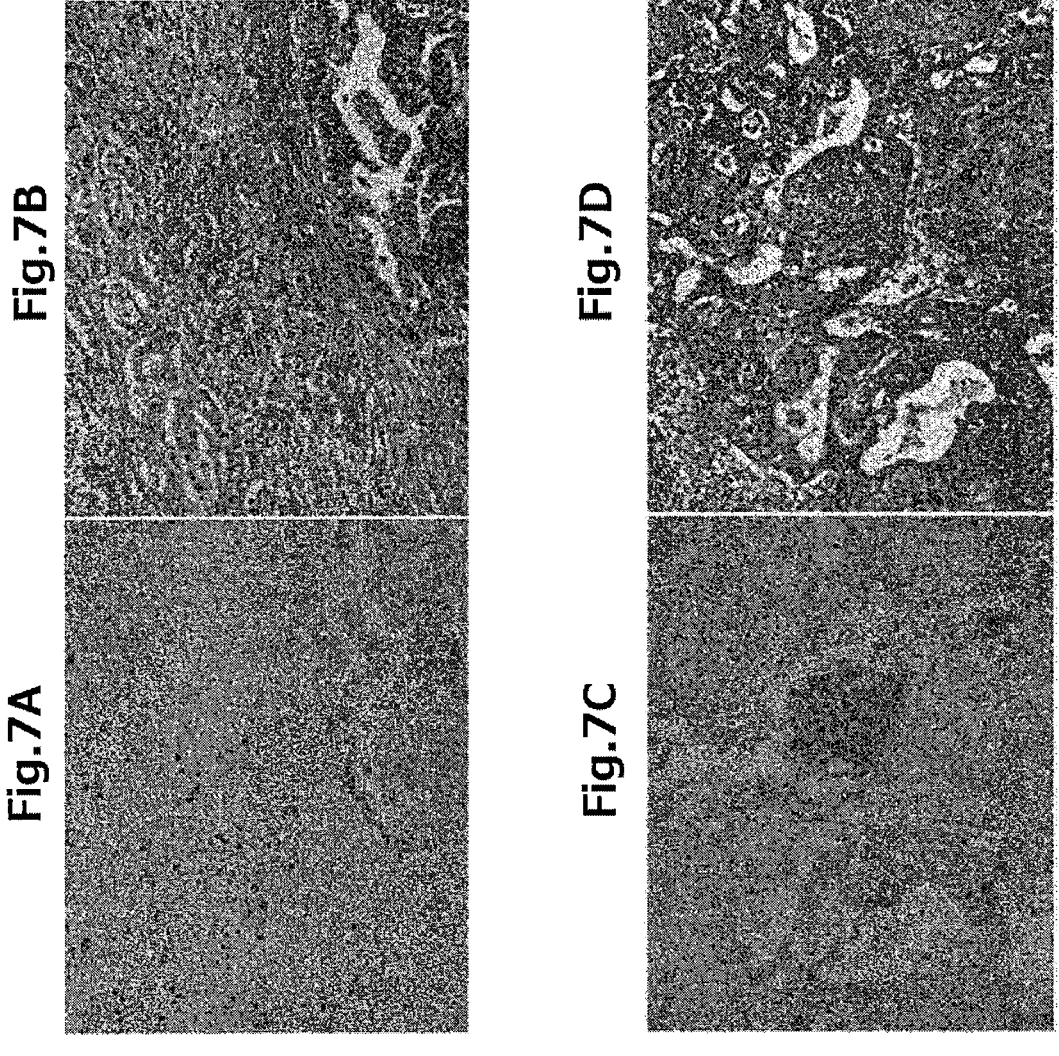
FIG. 7 First, 67 examples of cancer tissues of pancreatic cancer patient specimens were immunostained with anti-hTERT pT249 and determined to be positive when hTERT T249 phosphorylation (pT249) positive cells covered 10% or more of one field of view. The cancer tissues were classified into examples wherein pT249 detection was negative and examples wherein pT249 detection was positive and analyzed clinicopathologically. Consequently, the staining positive rate was 59.7% (40 examples of 67 examples), and staining positive cases were more with a statistically significant difference in lymph node metastasis positive examples (p value<0.0001) (FIGS. 7A and 7C). Moreover, it was found that the three-year survival rate was significantly low in staining positive cases in the analysis of operable cases (47 cases) (p value<0.05). It was observed that low differentiated adenocarcinoma components were stained more strongly than highly differentiated adenocarcinoma components also in the staining of specimens of the same patient (FIGS. 7A and 7B), and that squamous cell carcinoma components were stained strongly in adenosquamous carcinoma which is a poor prognostic pancreatic cancer (FIGS. 7C and 7D). These showed that T249 phosphorylation itself functioned as a poor prognostic predictive factor also in pancreatic cancer.

Clinical Information Analysis by Immunostaining Liver Cancer and Pancreatic Cancer Patient Specimens A specimen was stained using Envision+ kits (Dako) according to the attached manual. After formalin fixation, the paraffin embedded thinly sliced patient specimen was deparaffinized, hydrophilization-treated again and then autoclave-treated (at 120° C. for 5 minutes) using a citrate buffer (Dako, pH 6) to perform antigen activation treatment. The specimen was treated with a blocking buffer attached to the kits for 15 minutes, then reacted with the anti-hTERT pT249 antibody (1:250) at 4° C. for 8 hours, visualized with DAB+ substrate chromogen attached to the kits and microscopically examined. A specimen in which staining positive cells exist at 10% or more of one field of view in examination through the microscope with a magnifying power of 200 was determined as a "positive specimen." FIGS. 6 and 7 show the results.

Figure 8:
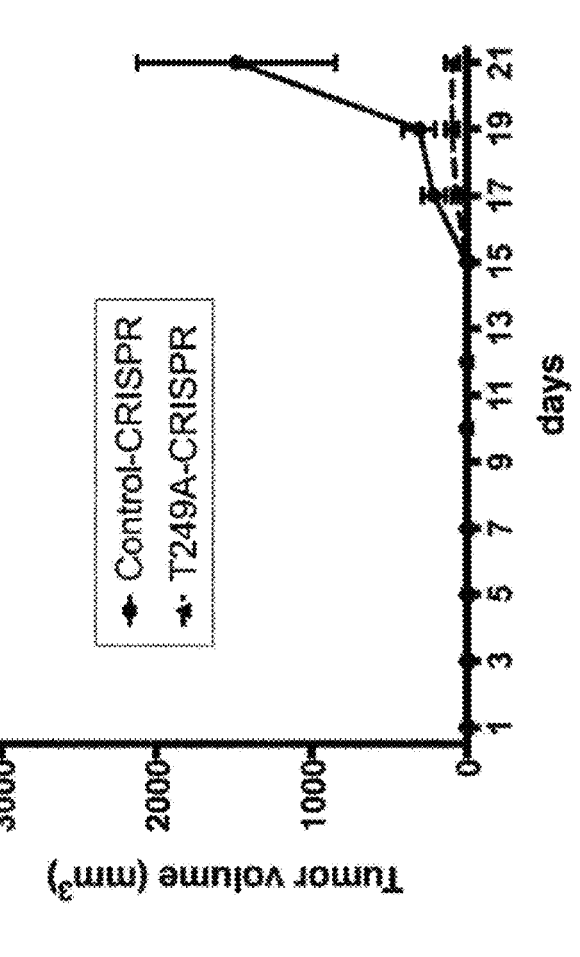
FIG. 8 T249A-CRISPR cells (T249A-CRISPR), wherein T249 in internal hTERT in 293T cells was replaced with alanine, which is a phosphorylation inactive amino acid, using CRISPR-Cas9 genome editing techniques were prepared. Only PuroCas9 was introduced into control cells (Control-CRISPR). Then, $1 \times 10^5$ T249A-CRISPR cells and $1 \times 10^5$ Control-CRISPR cells were hypodermically transplanted to NOD/SCID mice, respectively. It was observed that tumorigenicity was remarkably suppressed in the T249A-CRISPR cells. Since the T249A-CRISPR cells were cells wherein T249 was replaced with alanine, and phosphorylation did not occur thereby, it was confirmed that T249 phosphorylation was important for tumor formation.

Preparation of Mutant 293T Cell Line in which Amino Acid was Replaced with Phosphorylation Inactive Amino Acid Using CRISPR-Cas9 Genome Editing Techniques A T249A-CRISPR cell line in which threonine 249 in the internal hTERT protein in the 293T cell line was replaced with alanine, which was a phosphorylation inactive amino acid, using CRISPR-Cas9 genome editing techniques was prepared. First, a guide RNA sequence (AGCCG-GAGCGGACGCCCGTTGGG SEQ ID NO: 20, the underlined ACG is a codon encoding threonine) targeting the vicinity of the threonine 249 in hTERT was introduced into a plasmid vector which expressed Cas9, which was a genome editing enzyme, (PuroCas9) to prepare PuroCas9-hTERT. hTERT DNA having 223 bases including a target amino acid site (ACG encoding threonine is replaced with GCC encoding alanine) was introduced into a donor vector to replace the threonine 249 with alanine. These two plasmid vectors (PuroCas9-hTERT and the donor vector) were introduced into 293T cells using a transgenic reagent FuGene HD. Only PuroCas9 was introduced into control cells (Control-CRISPR). Since PuroCas9 contains a puromycin-resistant gene, cells into which PuroCas9 was introduced has puromycin resistance. The cells into which the plasmid vectors were introduced were drug-selected by puromycin treatment, and single cells were isolated. The Genome DNAs of the isolated cells were extracted, and the sequence replacement of the target site was confirmed by cutting with a restriction enzyme and Sanger sequencing. The results are shown in FIGS. 8 and 9.

The invention claimed is:

1. An isolated human telomerase reverse transcriptase (TERT) or a fragment thereof, comprising a part of an amino acid sequence corresponding to the amino acid sequence set forth in SEQ ID NO: 17, wherein the TERT and the part comprise an amino acid corresponding to T249 in the amino acid sequence set forth in SEQ ID NO: 17, (i) wherein the amino acid corresponding to T249 in the TERT or the fragment is replaced with alanine (A), wherein the TERT and the fragment have a telomere elongation enzyme activity, and wherein the TERT or the fragment has a reduced RNA-dependent RNA polymerase (RdRP) activity, compared to a TERT having threonine at position corresponding to T249.

2. An isolated human telomerase reverse transcriptase (TERT) or a fragment thereof, comprising a part of an amino acid sequence corresponding to the amino acid sequence set forth in SEQ ID NO: 17, wherein the TERT and the part comprise an amino acid corresponding to T249 in the amino acid sequence set forth in SEQ ID NO: 17, (ii) wherein the amino acid corresponding to T249 in the TERT or the fragment is replaced with glutamic acid (E), wherein the TERT and the fragment have a telomere elongation enzyme activity, and wherein the TERT or the fragment has an increased RNA-dependent RNA polymerase (RdRP) activity, compared to a TERT having threonine at position corresponding to T249.

3. The isolated human telomerase reverse transcriptase (TERT) of claim 1.

4. The isolated human telomerase reverse transcriptase (TERT) of claim 2.

* * * * *